（12）United States Patent
Min et al.

(10) Patent No.: US 7,225,015 B1
(45) Date of Patent: May 29, 2007

(54) SYSTEM AND METHOD FOR DETECTING CARDIAC ISCHEMIA BASED ON T-WAVES USING AN IMPLANTABLE MEDICAL DEVICE

(75) Inventors: Xiaoyi Min, Thousand Oaks, CA (US); Yougandh Chitre, Valencia, CA (US); Jeffery D. Snell, Chatsworth, CA (US); Gene A. Bornzin, Simi Valley, CA (US); Jong Kil, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 399 days.

(21) Appl. No.: 10/603,398

(22) Filed: Jun. 24, 2003

(51) Int. Cl.
*A61B 5/0468* (2006.01)

(52) U.S. Cl. ................ 600/517; 600/516

(58) Field of Classification Search .......... 600/508, 600/513, 516, 517, 509
See application file for complete search history.

(56) References Cited

U.S. PATENT DOCUMENTS

| | | | |
|---|---|---|---|
| 3,828,768 A | 8/1974 | Douglas | |
| 4,674,509 A | 6/1987 | DeCote, Jr. | |
| 4,679,144 A | 7/1987 | Cox et al. | |
| 4,799,486 A | 1/1989 | DuFault | |
| 4,974,162 A | 11/1990 | Siegel et al. | 364/413.06 |
| 5,113,869 A | 5/1992 | Nappholz et al. | 128/696 |
| 5,135,004 A | 8/1992 | Adams et al. | 128/696 |
| 5,148,812 A * | 9/1992 | Verrier et al. | 600/517 |
| 5,159,932 A * | 11/1992 | Zanetti et al. | 600/508 |
| 5,199,428 A | 4/1993 | Obel et al. | 128/419 C |
| 5,203,326 A | 4/1993 | Collins | 128/419 PG |
| 5,213,106 A | 5/1993 | Lerner | |
| 5,313,953 A | 5/1994 | Yomtov et al. | 128/696 |
| 5,365,426 A | 11/1994 | Siegel et al. | 364/413.06 |
| 5,531,768 A | 7/1996 | Alferness | |
| 5,560,368 A | 10/1996 | Berger | 128/703 |
| 5,560,370 A * | 10/1996 | Verrier et al. | 600/518 |
| 5,643,327 A | 7/1997 | Dawson et al. | 607/24 |
| 5,792,065 A * | 8/1998 | Xue et al. | 600/516 |
| 5,978,710 A | 11/1999 | Prutchi et al. | |
| 6,016,443 A | 1/2000 | Ekwall et al. | 600/519 |
| 6,021,350 A | 2/2000 | Mathson | 607/17 |
| 6,081,747 A | 6/2000 | Levine et al. | 607/9 |
| 6,108,577 A | 8/2000 | Benser | 600/517 |
| 6,112,116 A | 8/2000 | Fischell et al. | 600/517 |
| 6,115,628 A | 9/2000 | Stadler et al. | 600/517 |
| 6,128,526 A | 10/2000 | Stadler et al. | 600/517 |
| 6,155,267 A | 12/2000 | Nelson | |
| 6,233,486 B1 | 5/2001 | Ekwall et al. | 607/17 |
| 6,256,538 B1 | 7/2001 | Ekwall | 607/17 |
| 6,264,606 B1 | 7/2001 | Ekwall et al. | 600/300 |

(Continued)

*Primary Examiner*—George R. Evanisko
*Assistant Examiner*—Michael Kahelin

(57) ABSTRACT

A technique is provided for detecting episodes of cardiac ischemia based on an examination of the total energy of T-waves. Since cardiac ischemia is often a precursor to acute myocardial infarction (AMI) or ventricular fibrillation (VF), the technique thereby provides a method for predicting the possible onset of AMI or VF. Briefly, the technique integrates internal electrical cardiac signals occurring during T-waves and then compares the result against a running average. If the result exceeds the average by some predetermined amount, ischemia is thereby detected and a warning signal is provided to the patient. The maximum slope of the T-wave is also exploited. Techniques are also set forth herein for reliably detecting T-waves, which help prevent P-waves from being misinterpreted as T-waves on unipolar sensing channels. The T-wave detection technique may be used in conjunction with ischemia detection or for other purposes.

17 Claims, 12 Drawing Sheets

U.S. PATENT DOCUMENTS

| | | |
|---|---|---|
| 6,272,379 B1 | 8/2001 | Fischell et al. ................. 607/5 |
| 6,361,503 B1 | 3/2002 | Starobin et al. ............ 600/508 |
| 6,381,493 B1 * | 4/2002 | Stadler et al. ................. 607/9 |
| 6,501,983 B1 | 12/2002 | Natarajan et al. ........... 600/517 |
| 6,539,259 B1 | 3/2003 | Weinberg et al. |
| 6,604,000 B2 | 8/2003 | Lu ............................. 607/17 |
| 6,609,023 B1 | 8/2003 | Fischell et al. ............. 600/515 |
| 6,615,075 B2 * | 9/2003 | Mlynash et al. ............. 600/513 |
| 6,823,213 B1 * | 11/2004 | Norris et al. .................. 607/9 |
| 2002/0151807 A1 * | 10/2002 | Goldin ....................... 600/509 |
| 2003/0013974 A1 | 1/2003 | Natarajan et al. ............ 600/481 |
| 2003/0045805 A1 | 3/2003 | Sheldon et al. ............. 600/513 |
| 2003/0060724 A1 * | 3/2003 | Thiagarajan et al. ........ 600/515 |
| 2003/0060854 A1 | 3/2003 | Zhu ............................. 607/25 |
| 2003/0073914 A1 | 4/2003 | Taha et al. ................... 600/509 |
| 2003/0144700 A1 | 7/2003 | Brown et al. ................. 607/14 |
| 2003/0153956 A1 | 8/2003 | Park et al. .................... 607/17 |
| 2003/0208129 A1 | 11/2003 | Beker et al. ................ 600/509 |
| 2004/0077941 A1 | 4/2004 | Reddy et al. ............... 600/428 |
| 2004/0249420 A1 | 12/2004 | Olson et al. ................... 607/9 |

\* cited by examiner

SYSTEM AND METHOD FOR DETECTING CARDIAC ISCHEMIA BASED ON T-WAVES USING AN IMPLANTABLE MEDICAL DEVICE

CROSS REFERENCE TO RELATED APPLICATIONS

This application is related to copending U.S. patent applications: 1) Ser. No. 10/606,299, filed Jun. 24, 2003, titled "System and Method for Detecting Cardiac Ischemia Based on T-Waves Using an Implantable Medical Device"; and 2) Ser. No. 10/603,429, filed Jun. 24, 2003, titled "System and Method for Detecting Cardiac Ischemia Using an Implantable Medical Device," which are incorporated herein by reference.

FIELD OF THE INVENTION

The invention generally relates to implantable medical devices such as pacemakers and implantable cardioverter/defibrillators (ICDs) and, in particular, to techniques for detecting cardiac ischemia using such devices.

BACKGROUND OF THE INVENTION

Cardiac ischemia is a condition whereby heart tissue does not receive adequate amounts of oxygen and is usually caused by a blockage of an artery leading to heart tissue. If sufficiently severe, cardiac ischemia results in an acute myocardial infarction (AMI), also referred to as a heart attack. With AMI, a substantial portion of heart muscle ceases to function because it no longer receives oxygen, usually due to significant blockage of the coronary artery. Generally, AMI occurs when plaque (such as fat, cholesterol, and calcium) builds up and then ruptures in the coronary artery, allowing a blood clot or thrombus to form. Eventually, the blood clot completely blocks the coronary artery and so heart tissue beyond the blockage no longer receives oxygen and the tissue dies. In many cases, an AMI proves fatal because too much tissue is damaged to allow continued functioning of the heart muscle. Indeed, AMI is a leading cause of death here in the United States and worldwide. In other cases, although the AMI itself may not be fatal, it strikes while the victim is engaged in potentially dangerous activities, such as driving vehicles or flying airplanes, and the severe pain and possible loss of consciousness associated with AMI results in fatal accidents. Even if the victim survives the AMI, quality of life may thereafter be severely restricted.

Often AMI is preceded by episodes of cardiac ischemia that are not sufficiently serious to cause actual permanent injury to the heart tissue. Nevertheless, these episodes are often precursors to AMI. Episodes of cardiac ischemia may also trigger certain types of arrhythmias that may prove fatal, particularly ventricular fibrillation (VF) wherein the ventricles of the heart beat chaotically resulting in little or no net flow of blood from the heart to the brain and other organs. Indeed, serious episodes of cardiac ischemia (referred to herein as acute myocardial ischemia) typically result in either a subsequent AMI or VF, often within one to twenty-four four hours, sometimes within only a half an hour or less.

Accordingly, it would be highly desirable to provided a technique for reliably detecting acute myocardial ischemia so that the victim may be warned and medical attention sought. If properly warned, surgical procedures may be implemented to locate and remove the growing arterial blockage or anti-thrombolytic medications may be administered. At the very least, advanced warning would allow the victim to cease activities that might result in a fatal accident. Moreover, in many cases, AMI or VF is triggered by strenuous physical activities and so advanced warning would allow the victim to cease such activities, possibly preventing AMI or VF from occurring.

Many patients at risk of cardiac ischemia have pacemakers, ICDs or other medical devices implanted therein. Accordingly, techniques have been proposed for detecting cardiac ischemia using implanted medical devices. In particular, techniques have been developed for analyzing internal electrocardiogram (IEGM) signals in an effort to detect cardiac ischemia. See, as examples, the following U.S. Pat. No.: 5,113,869 to Nappholz; U.S. Pat. No. 5,135,004 to Adams et al.; U.S. Pat. No. 5,199,428 to Obel et al.; U.S. Pat. No. 5,203,326 to Collins; U.S. Pat. No. 5,313,953 to Yomtov et al; U.S. Pat. No. 6,501,983 to Natarajan, et al.; U.S. Pat. Nos. 6,016,443, 6,233,486, 6,256,538, and 6,264,606 to Ekwall; U.S. Pat. No. 6,021,350 to Mathson; U.S. Pat. No. 6,112,116 and 6,272,379 to Fischell et al; U.S. Pat. Nos. 6,128,526, 6,115,628 and 6,381,493 to Stadler et al; and U.S. Pat. No. 6,108,577 to Benser. Most ischemia detection techniques seek to detect ischemia by identifying changes in the ST segment of the IEGM that are manifest during cardiac ischemia. The ST segment represents the portion of the cardiac signal between ventricular depolarization (also referred to as an R-wave to QRS complex) and ventricular repolarization (also referred to as a T-wave). The ST segment usually follows an atrial depolarization (also referred to as a P-wave.) Strictly speaking, P-waves, R-waves and T-waves are features of a surface electrocardiogram (EKG). For convenience, herein, the terms R-wave, T-wave and P-wave are used to refer to the corresponding internal signal component as well.

Problems, however, arise when attempting to detect cardiac ischemia using ST segments. Most pacemakers and ICDs initially route electrical cardiac signals through highpass filters to eliminate direct current (DC) components so that the signals can be more easily and reliably analyzed to detect relatively high frequency components such as P-waves and R-waves. However, ST segments primarily consist of very low-frequency signals. So, to permit ST segments to be analyzed for ischemia detection purposes, the highpass filter must be configured to have a sufficiently low cutoff frequency (typically about 0.1 Hz) to allow the low frequency components of the ST segments to pass through the filter. Unfortunately, highpass filters requiring low cutoff frequencies are not well suited for use within implantable medical devices. In particular, such filters require very large capacitors, which add significantly to the size and weight of the implantable device. In addition, because the ST segment primarily consists of low-frequency signals, techniques based upon an analysis of those segments may not be particularly reliable. Accordingly, it would be desirable to provide techniques for detecting cardiac ischemia that do not exploit the ST segment.

One such technique is set forth In U.S. patent application Ser. No. 10/603,429, of Wang et al., entitled "System And Method For Detecting Cardiac Ischemia Using An Implantable Medical Device", filed contemporaneously herewith, which assigned to the assignee of rights to the present application and is incorporated by reference herein. Rather than examine the ST segment, the technique of Wang et al. instead examines post-T-wave segments, i.e. that portion of the cardiac signal immediately following the T-wave.

Although the technique of Wang et al. is very effective in detecting cardiac ischemia while avoiding problems associated with ST segments, it would also be desirable to provide additional or alternative techniques that do not exploit the ST segment.

An alternative to examining the post T-wave segment is to instead examine the T-wave itself. According to some of the patents cited above, various T-wave-based techniques have been developed that exploit: T-wave inversion; changes in the duration or amplitude of T-waves; changes in the rate of rise/fall of the T-wave; or changes in T-wave uniformity. However, it does not appear that any reliable cardiac ischemia detection techniques have been developed that examine the total energy of the T-wave. In contrast, techniques that merely examine the amplitude of a T-wave do not gain a true measure of T-wave energy. Accordingly, it would be desirable to provide a cardiac ischemia detection technique that is based on the total energy of T-waves and it is to that end that aspects of the invention are primarily directed. Nor does it appear that any cardiac ischemia detection techniques have been developed that examine maximum T-wave slope in combination with total T-wave energy and other aspects of the invention are directed to that end as well.

One concern with T-wave-based ischemia detection techniques is that it can sometimes be difficult to distinguish true T-waves from P-waves appearing within channels used to sense ventricular signals. This problem can occur, for example, when using a unipolar lead mounted in the ventricles to sense ventricular signals and a bipolar lead mounted in the atria to sense atrial signals. The problem can also arise when using a bipolar lead mounted in the atria to sense both ventricular signals and atrial signals, i.e. ventricular signals are sensed by using the bipolar lead in a unipolar mode (i.e. ring to case sensing or tip to case sensing) whereas the atrial signals are sensed by using the same bipolar lead in bipolar mode (i.e. tip to ring sensing). Accordingly, it would also be desirable to provide for improved T-wave detection techniques, either for use with cardiac ischemia detection or for other purposes, and it is to that end that still other aspects of the invention are directed.

SUMMARY OF THE INVENTION

In accordance with a first aspect of the invention, an improved technique is provided for detecting the onset of a cardiac ischemia, such as those leading to AMI, using an implantable medical device. A plurality of ventricular repolarization events (i.e. T-waves) are detected within cardiac signals sensed by the device. Then energy values of the plurality of T-waves are determined and cardiac ischemia is detected based on the energy values of the T-waves. By detecting cardiac ischemia based on energy values of the T-waves rather than on merely their duration or peak amplitude, it is believed that a more reliable detection of cardiac ischemia is achieved.

In an exemplary embodiment, the energy of a T-wave is determined by calculating:

$$E_{T-Wave} = \sum_{n=Tstart}^{Tend} s(n)$$

where s(n) is a digitized version of the cardiac signal, $T_{start}$ and $T_{end}$ are start and end points, respectively, of a T-wave segment, and n represents individual samples of the digitized signal.

In addition, in the exemplary embodiment, detection of cardiac ischemia depends, in part, on whether individual T-waves are the result of a paced beat or a sinus beat. For sinus beats, a peak amplitude of the R-wave preceding the T-wave is determined and then used to normalize the T-wave energy. A running average of normalized T-wave energy values for the sinus beats is maintained. A difference is calculated between the normalized energy of the latest T-wave and the running average of other sinus beat T-waves. The difference is compared to a sinus beat-based detection threshold and, if it exceeds the threshold for some specified number of beats, cardiac ischemia is thereby detected. For paced beats, a measure of the evoked response is derived and then used to normalize the T-wave energy. A running average of normalized T-wave energy values for paced beats is maintained. If the paced beat is not captured, the associated T-wave energy is zero. In any case, a difference is calculated between the energy of the latest T-wave and the running average of the paced-beat T-waves. The difference is compared to a paced beat-based detection threshold and, if it exceeds the threshold for some specified number of beats, cardiac ischemia is thereby also detected. In practice, since a mixture of both paced beats and sinus beats are expected, running averages are maintained for both paced beat and sinus beat T-wave energies and the detection of cardiac ischemia exploits both. In any case, by normalizing T-wave energies when needed and by comparing T-wave energies against running averages, the reliability of the detection of cardiac ischemia is further enhanced. The maximum slope of T-waves (i.e. max dV/dt) may also be determined and exploited in combination with total T-wave energy to help refine the detection of ischemia. Preferably, T-waves associated with ectopic beats and fused beats are ignored.

In accordance with a second aspect of the invention, an improved technique is provided for detecting T-waves, which helps prevent P-waves from being misinterpreted as T-waves on unipolar sensing channels. In one example, atrial bipolar signals are sensed using a bipolar lead mounted within the atria and unipolar signals are sensed using a lead mounted in the ventricles. In another example, atrial bipolar signals are again sensed using a bipolar lead mounted within the atria with the unipolar signals sensed using the same lead, but operating in a unipolar mode. In any case, P-waves are detected within the atrial bipolar signals, then used to eliminate P-waves from the unipolar signals to leave substantially only ventricular events therein. Then the ventricular events are examined to identify T-waves. By first detecting P-waves within atrial bipolar signals and then using them to eliminate P-waves from the unipolar signals, the reliability of T-wave detection is improved. The improved T-wave detection technique is well suited for detecting T-waves for use in ischemia detection but may also be used for any other suitable purpose, such as in the detection of SVT (supraventricular tachycardia) and PVCs (premature ventricular contractions).

Thus, improved techniques are provided both for reliably detecting T-waves and for then detecting cardiac ischemia based on the T-waves. Other features, objects and advantages of the invention are set forth below.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Device

Figure 1:
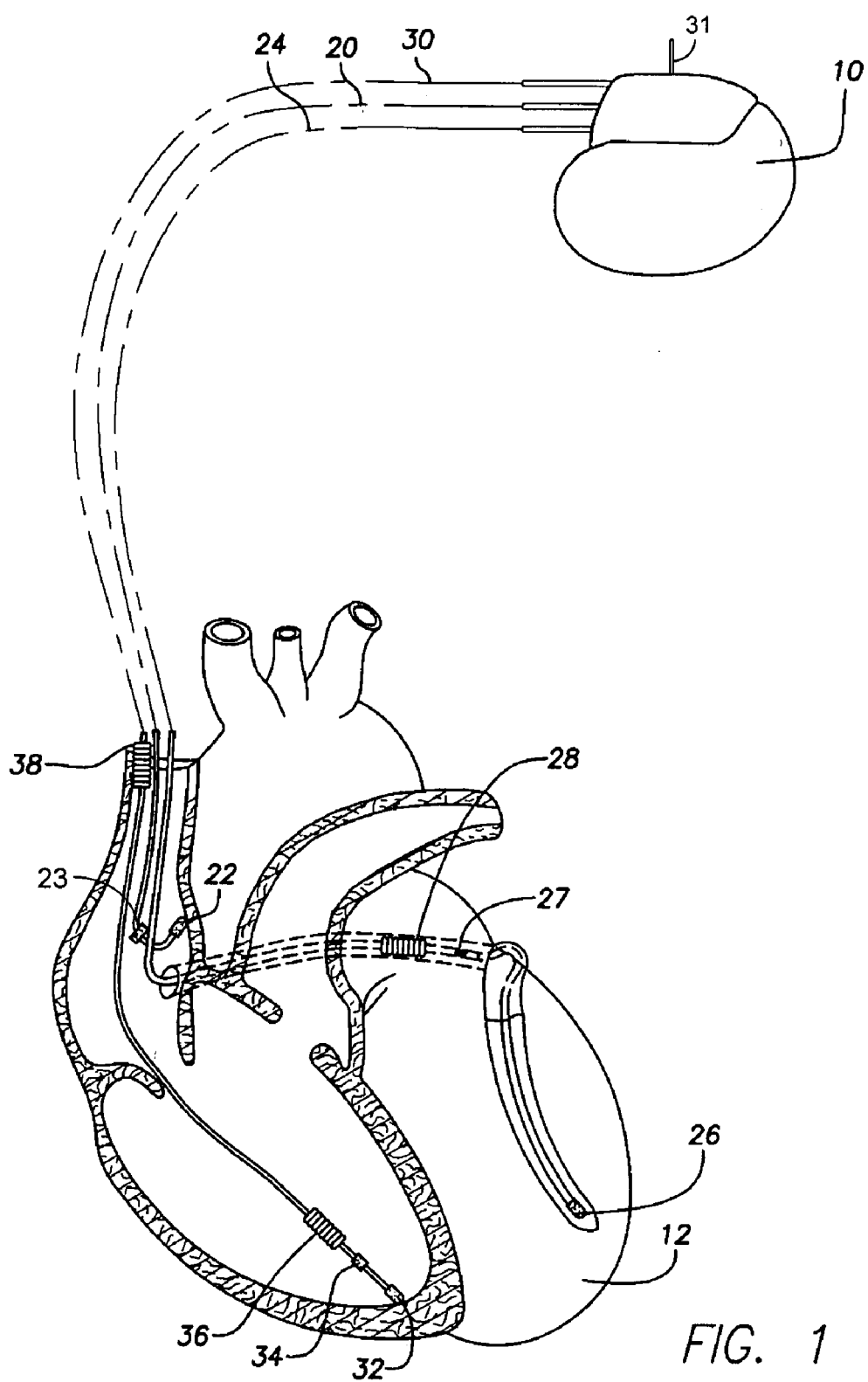
FIG. 1 is a simplified diagram illustrating an implantable stimulation device in electrical communication with at least three leads implanted into the heart of a patient for delivering multi-chamber stimulation and shock therapy including cardioversion therapy and overdrive pacing therapy.

As shown in FIG. 1, there is a stimulation device 10 in electrical communication with the heart 12 of a patient by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the right atrial appendage and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the heart by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart so as to place the right ventricular tip electrode 32 in the right ventricular apex so that the RV coil electrode is positioned in the right ventricle and the SVC coil electrode 38 is positioned in the superior vena cava. Accordingly, the right ventricular lead 30 is capable of receiving cardiac signals, and delivering stimulation in the form of pacing and shock therapy to the right ventricle. To provide a "tickle warning" signal, an additional electrode 31 is provided in proximity to the device can.

Figure 2:
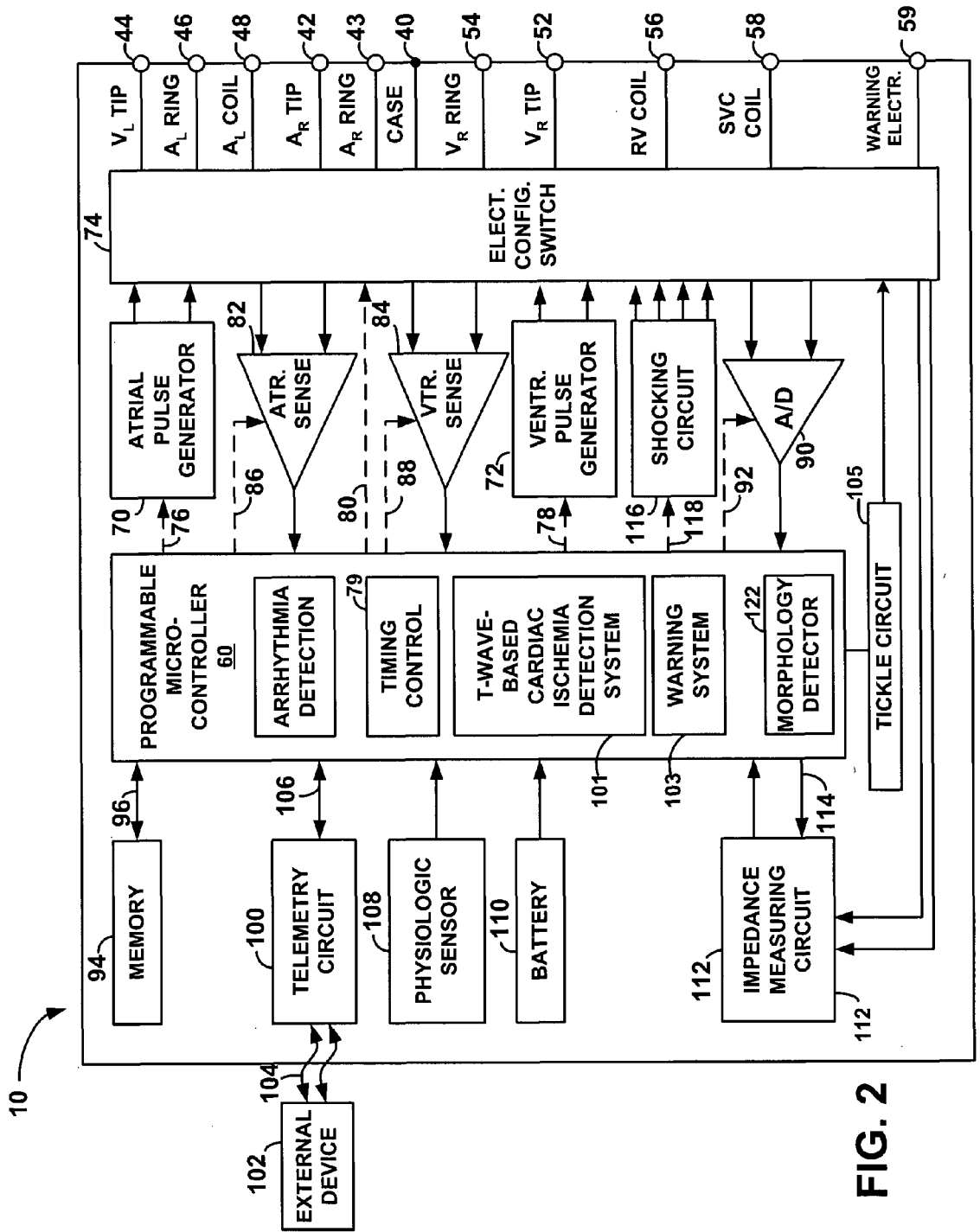
FIG. 2 is a functional block diagram of the implantable cardiac stimulation device of FIG. 1 illustrating basic elements of the stimulation device particularly including a cardiac ischemia detection system for detecting cardiac ischemia based primarily on T-wave signal energy.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56 and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively. To provide the "tickle warning" signal, an additional terminal 59 is provided for connection to the tickle warning electrode 31 of FIG. 1.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it detects the occurrence of an arrhythmia and automatically applies an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Finally, with regard to FIG. 2, microcontroller 60 includes a T-wave-based cardiac ischemia detection system 101 for controlling the detection of episodes of cardiac ischemia and a warning system 103 for controlling the delivery of warning signals to the patient. In particular, warning system 103 controls a tickle circuit 105 to generate a perceptible internal warning signal using tickle warning electrode 31 of FIG. 1.

Referring to the remaining figures, flow charts, graphs and other diagrams illustrate the operation and novel features of stimulation device 10 as configured in accordance with exemplary embodiments of the invention. In the flow charts, the various algorithmic steps are summarized in individual "blocks". Such blocks describe specific actions or decisions made or carried out as the algorithm proceeds. Where a microcontroller (or equivalent) is employed, the flow charts provide the basis for a "control program" that may be used by such a microcontroller (or equivalent) to effectuate the desired control of the stimulation device. Those skilled in the art may readily write such a control program based on the flow charts and other descriptions presented herein.

Overview of T-Wave-Based Cardiac Ischemia Detection

Figure 3:
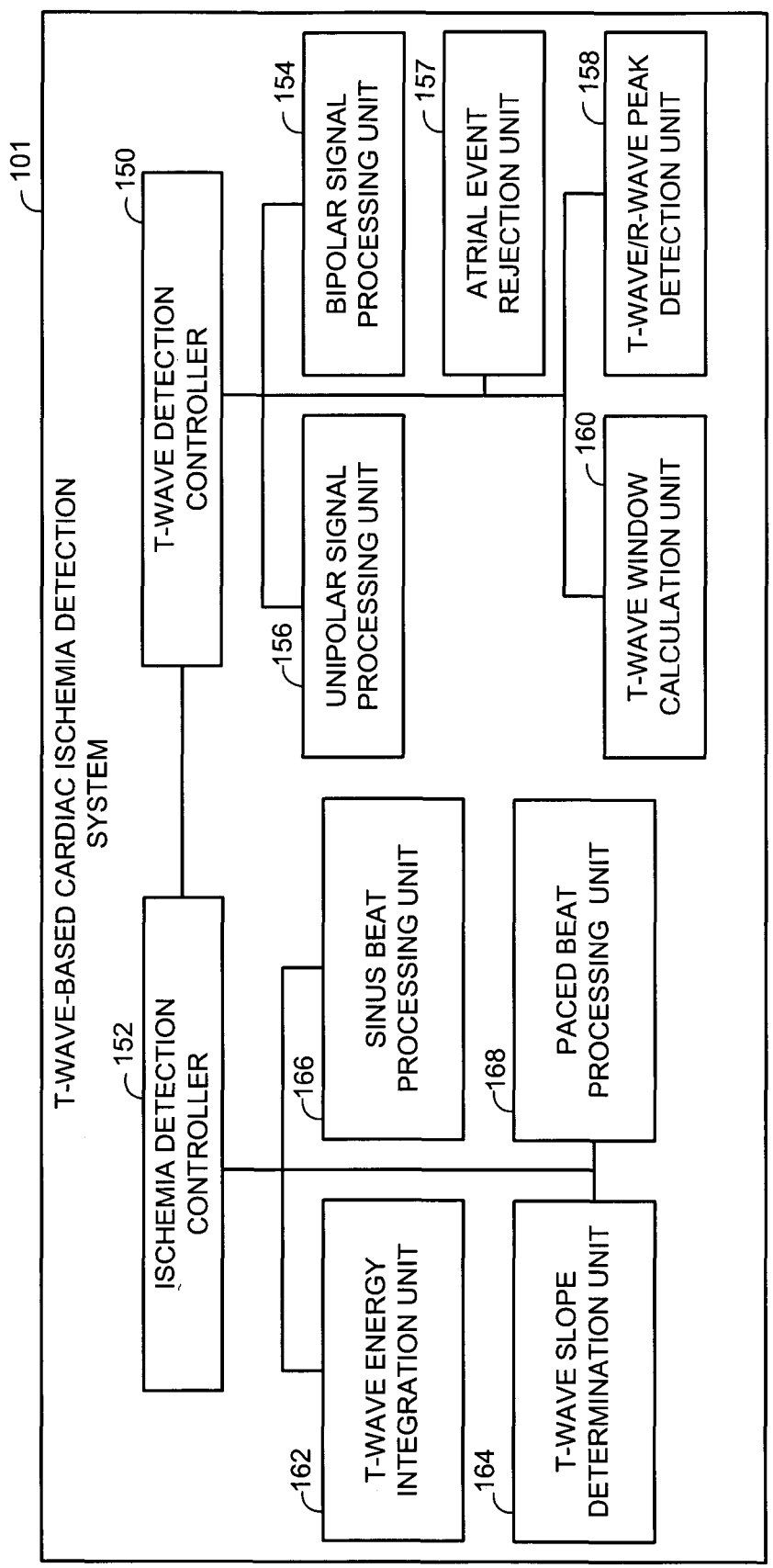
FIG. 3 is a functional block diagram of components of the cardiac ischemia detection system of FIG. 2.

FIG. 3 illustrates pertinent components of T-wave-based cardiac ischemia detection system 101 of the microcontroller or FIG. 2. Briefly, the system operates to detect T-waves within IEGM signals and then to detect the onset of an episode of cardiac ischemia based on an analysis of total energies and maximum slopes of the T-waves. To this end, detection system 101 includes both a T-wave detection controller 150 for coordinating components that identify T-waves within IEGM signals and a cardiac ischemia detection controller 152 for coordinating components that analyze the T-waves to detect the onset of ischemia. T-waves are detected using both an atrial bipolar signal processing unit 154 and a unipolar signal processing unit 156. Atrial events (i.e. P-waves) detected with the bipolar signals are then eliminated from the unipolar signals using an atrial event rejection unit 157. By eliminating atrial events from the unipolar signals, the unipolar signals thereby include only ventricular events, i.e. T-waves and R-waves. A T-wave/R-wave peak detection unit 158 examines the filtered unipolar signals to identify the peaks of T-waves and R-waves. A T-wave window calculation unit 160 specifies a T-wave location window based upon either the T-wave peak or the preceding R-wave peak. Once a T-wave window has been specified, a T-wave energy integration unit 162 calculates the energy associated with the T-wave while a T-wave slope determination unit 164 determines its maximum slope. Detection of the onset of the cardiac ischemia depends, in part, on whether each T-wave was a result of a sinus beat or a paced beat. Accordingly, both a sinus beat processing unit 166 and a paced beat processing unit 168 are provided. Note that, depending upon the implementation, not all of the components shown in FIG. 3 need be implemented as portions of the microcontroller. Rather, some or all of the components may be implemented as stand-alone devices within the overall implantable device or may be integrated with other device components. Hence, the invention is not limited to being implemented as shown in the figure.

Figure 4:
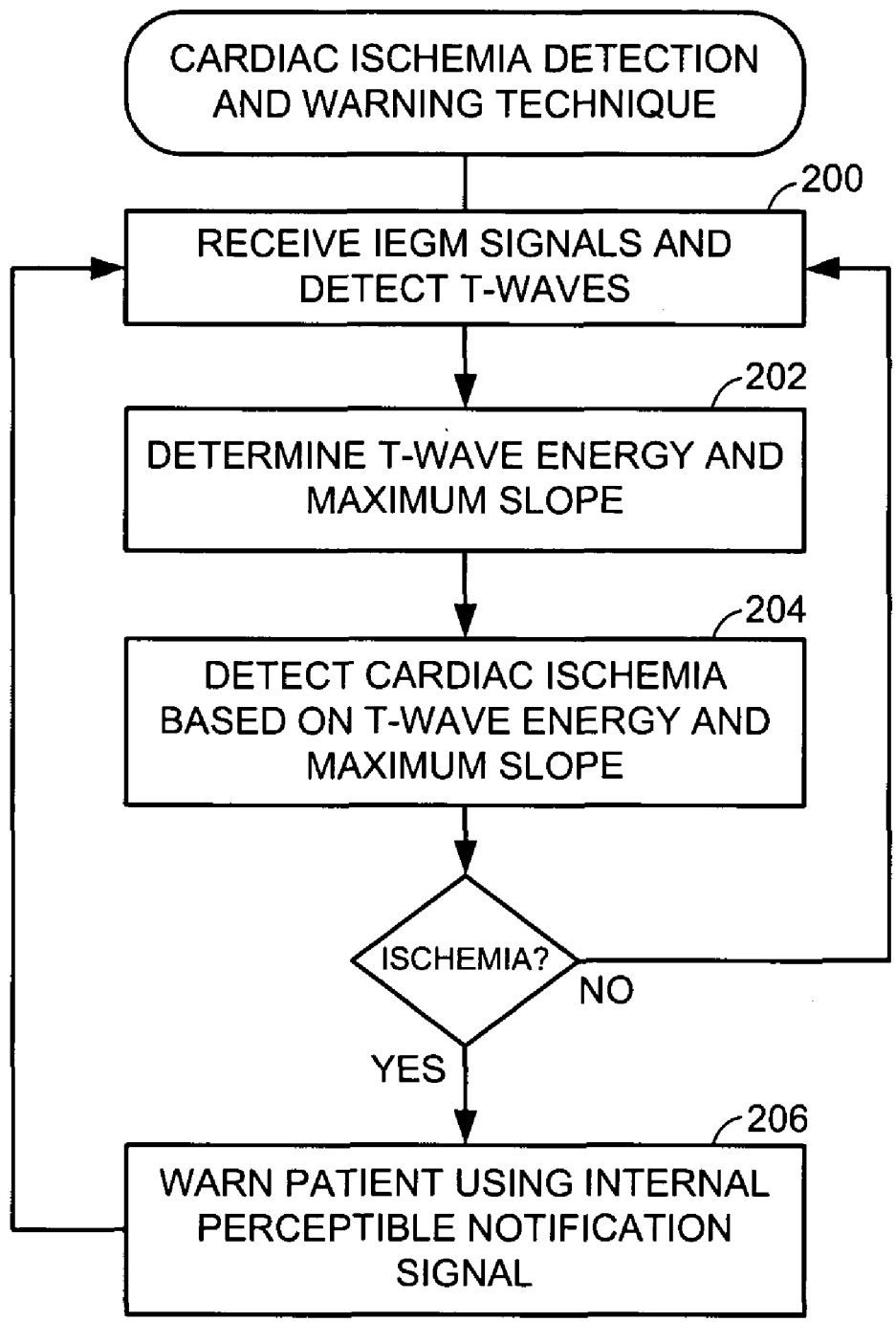
FIG. 4 is a flow chart providing an overview of an exemplary method performed by the detection system of FIG. 2 for detecting cardiac ischemia based primarily on T-wave signal energy.

FIG. 4 provides an overview of the cardiac ischemia detection technique performed by the ischemia detection system of FIG. 3. Initially, at step 200, IEGM signals are received and T-waves are detected under the control of the T-wave detection controller. Then, T-wave energy and maximum slope are determined, at step 202, using the energy integration unit and slope determination unit. At step 204, the onset of a cardiac ischemia is detected based upon the T-wave energy and maximum slope using the paced beat and sensed beat processing units. So long as no ischemia is detected, steps 200–204 are merely repeated. If ischemia is detected, however, the patient is warned of the ischemia by application of an internal perceptible "tickle" notification signal, at step 206. If the device is configured to generate warning signals for other arrhythmias, such as atrial fibrillation, the device preferably employs different notification signal frequencies for the different warnings so that the patient can properly distinguish between different warnings. In addition, warning signals may be transmitted using a short-range telemetry system to a handheld warning device using techniques described within the above-referenced patent application to Wang et al.

Figure 5:
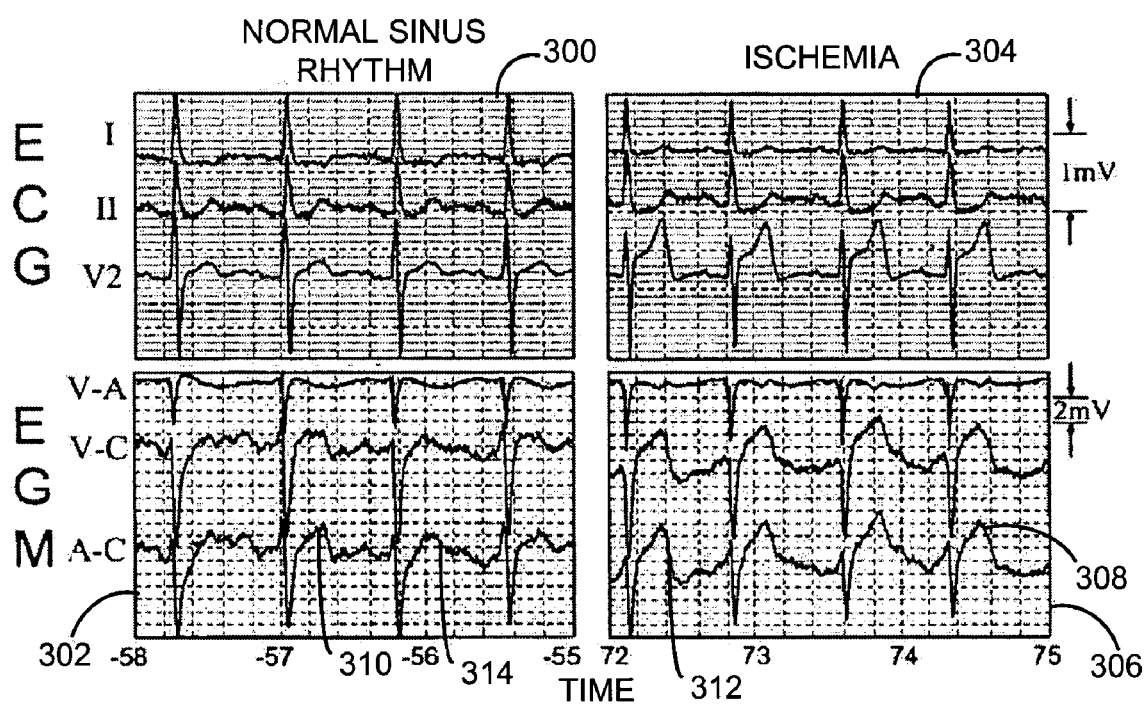
FIG. 5 is a graph illustrating IEGM signals processed by the method of FIG. 4 along with corresponding surface ECG signals for episodes of ischemia as well as for normal sinus rhythm.

Thus, the technique exploits both the total energies of individual T-waves and the maximum slopes of T-waves to detect cardiac ischemia. The effect of cardiac ischemia on both T-wave energy and T-wave maximum slope is illustrated in FIG. 5, which shows various conventional IEGM and surface EKG signal traces obtained from a canine test subject during normal sinus rhythm and during an episode of artificially-induced cardiac ischemia. More specifically, graph 300 illustrates various surface EKG signals during a normal sinus rhythm and graph 302 illustrates corresponding IEGM signals also during normal sinus rhythm. Graph 304 illustrates surface EKG signals during an artificially induced cardiac ischemia, generated by inflating a balloon within an artery leading to heart tissue. Graph 306 illustrates corresponding IEGM signals also during the artificially induced episode of cardiac ischemia. As can be seen, T-waves 308 during cardiac ischemia are much larger than T-waves 310 during normal sinus rhythm. Since T-waves are considerably larger during cardiac ischemia, the total energy within the T-waves (i.e. the integral or sum of the individual amplitude values of the signal during the T-wave) is considerably greater during cardiac ischemia then during a normal sinus rhythm. Hence, total T-wave energy provides a reliable indicator of cardiac ischemia. In addition, the maximum slope of each T-wave is considerably steeper during the episode of cardiac ischemia. Compare, for example, slope 312 of graph 306 against slope 314 of graph 302. Detection of a sharp maximum T-wave slope thereby helps confirm the detection of cardiac ischemia made based upon the T-wave energy. Alternatively, the maximum T-wave slope can be used as an independent indicator of cardiac ischemia, but it is believed to be more reliable when used in combination with total T-wave energy.

Figure 6:
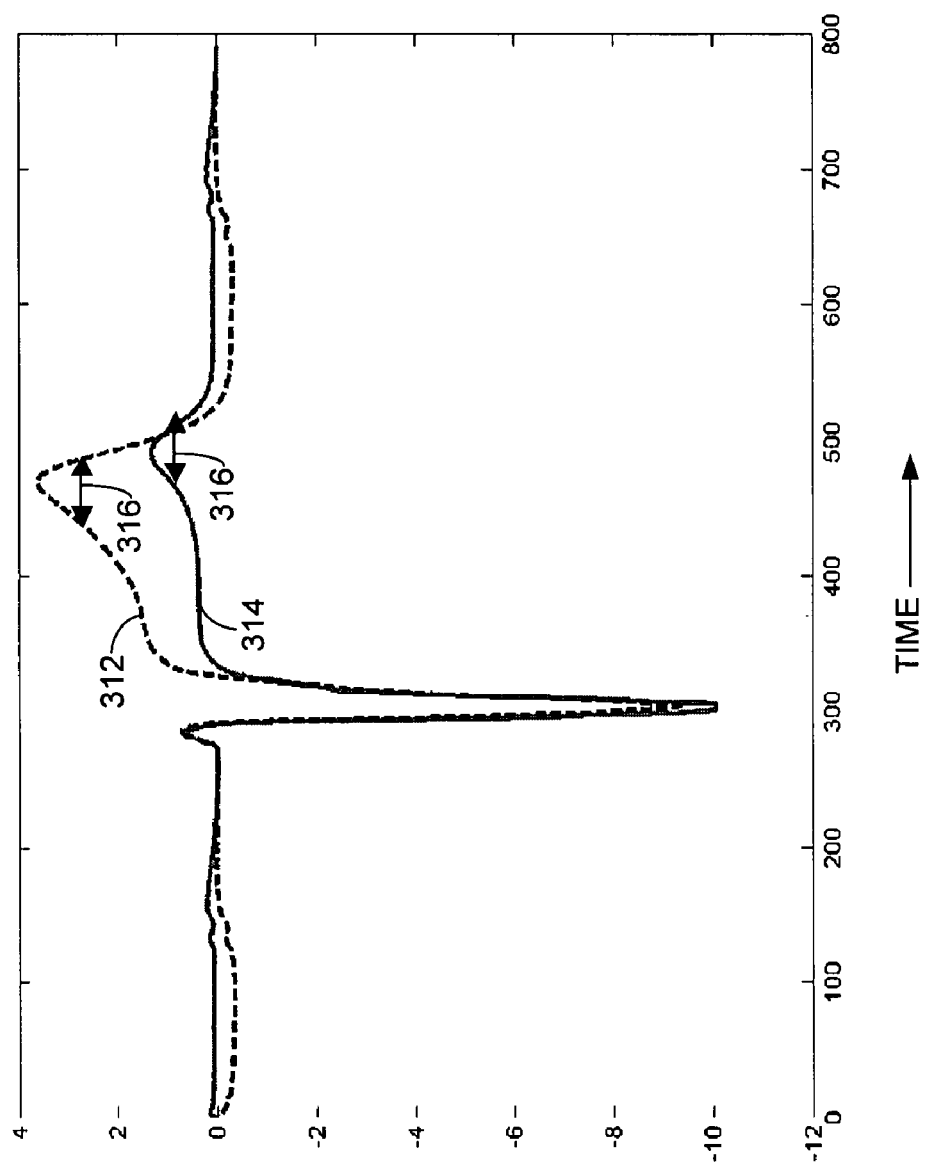
FIG. 6 is another graph illustrating IEGM signals processed by the method of FIG. 4 and particularly illustrating an increase in T-wave energy and in maximum T-wave slope during cardiac ischemia.

FIG. 6 provides a side-by-side comparison of a right ventricular ring IEGM for a single hear heart beat for normal sinus rhythm and for cardiac ischemia, again obtained from a canine test subject. More specifically, solid line 314 illustrates the heart beat during normal sinus rhythm (i.e. baseline) whereas dashed line 312 illustrates the heart beat obtained five minutes after artificial occlusion of the left anterior descending coronary artery (LAD). In the figures, reference numeral 316 identifies a T-wave window, centered at each T-wave peak, in which the total energy and maximum slope is actually calculated. The T-wave window (TW) is 60 milliseconds (ms) in both cases. The integral of T-wave energy within the window was determined to be 364 □V-seconds during the ischemia but only 124 □V-seconds during normal sinus rhythm. Max dV/dt during ischemia was determined to be −0.22 V/second but only −0.08 V/second during normal sinus rhythm. Note that maximum dV/dt here refers to the maximum positive or maximum negative slope, whichever is larger in magnitude.

T-Wave Detection

Figure 7:
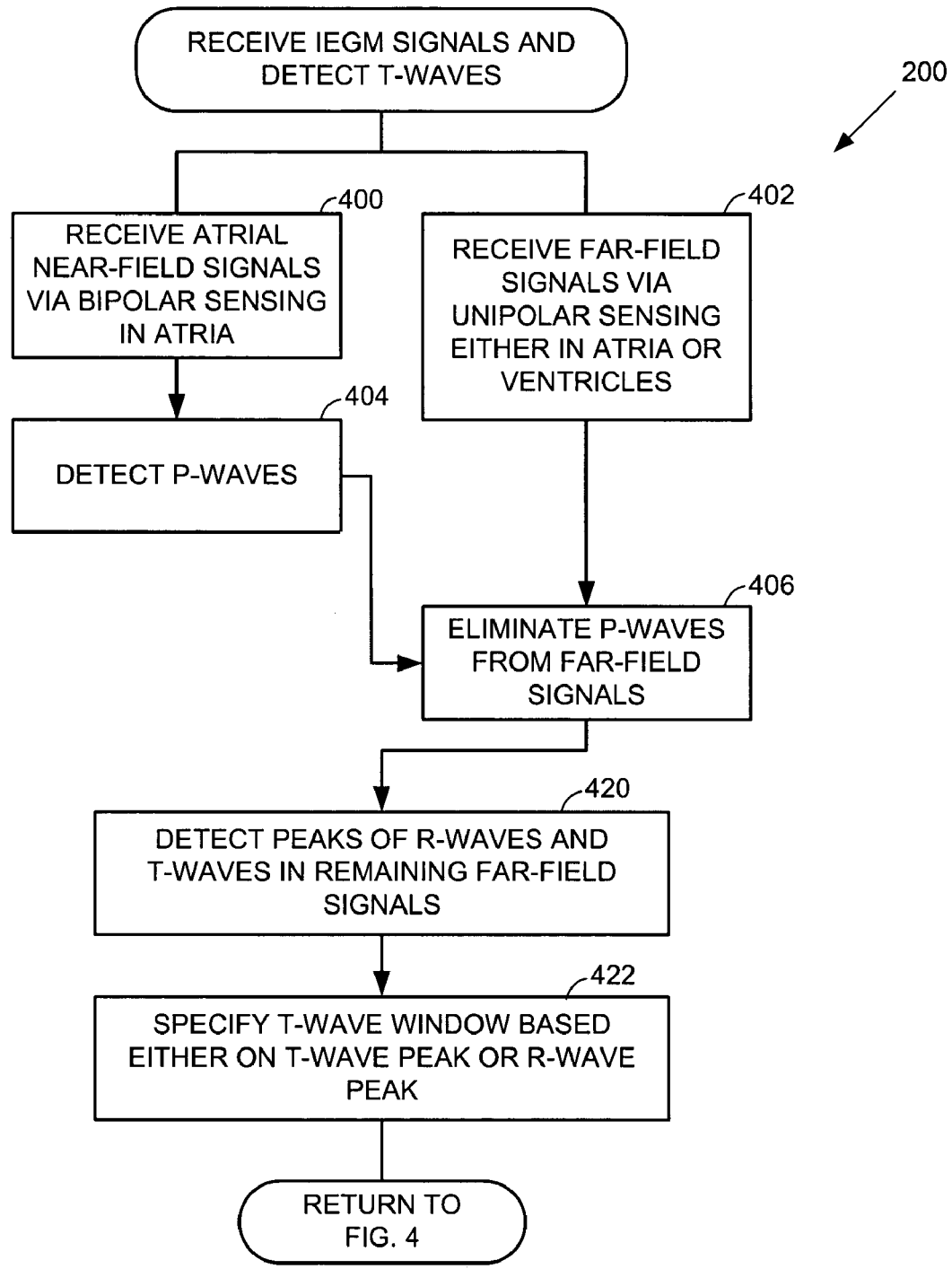
FIG. 7 is a flow chart illustrating an exemplary method for reliably detecting T-waves using both bipolar and unipolar sensing channels, either for use with the method of FIG. 4 or for other purposes.
Figure 8:
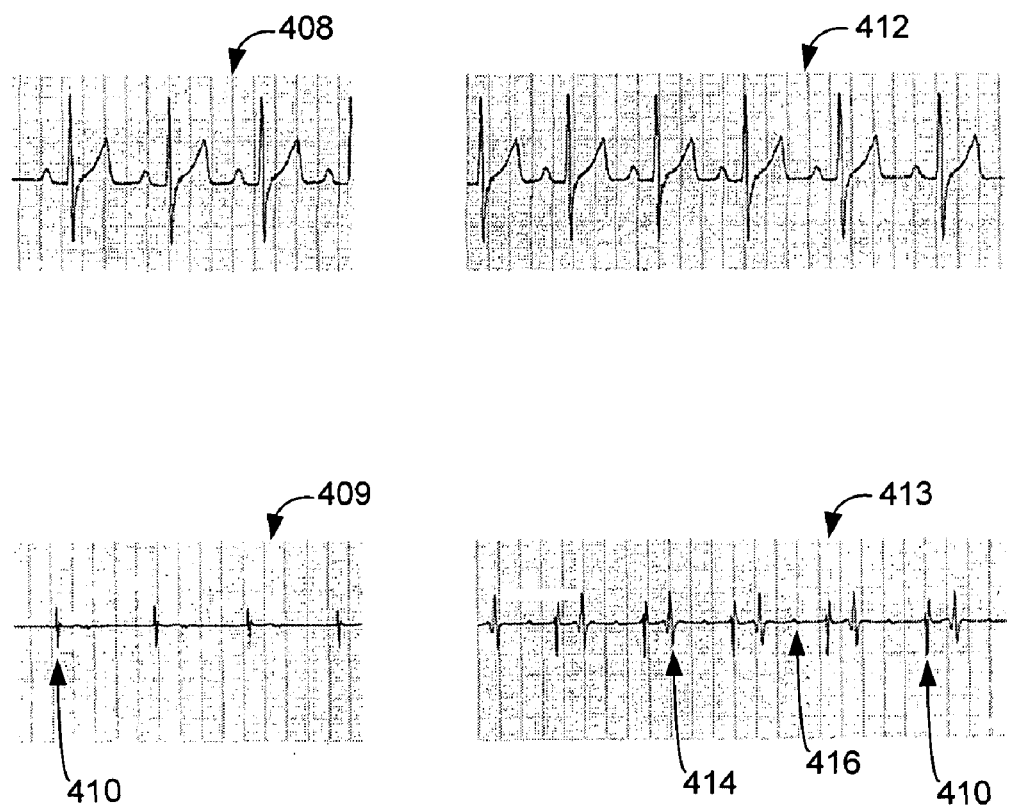
FIG. 8 is a graph illustrating both bipolar and unipolar IEGM signals for use with the method of FIG. 7, along with corresponding surface ECG signals, and particularly illustrating P-waves sensed within unipolar channel signals.
Figure 9:
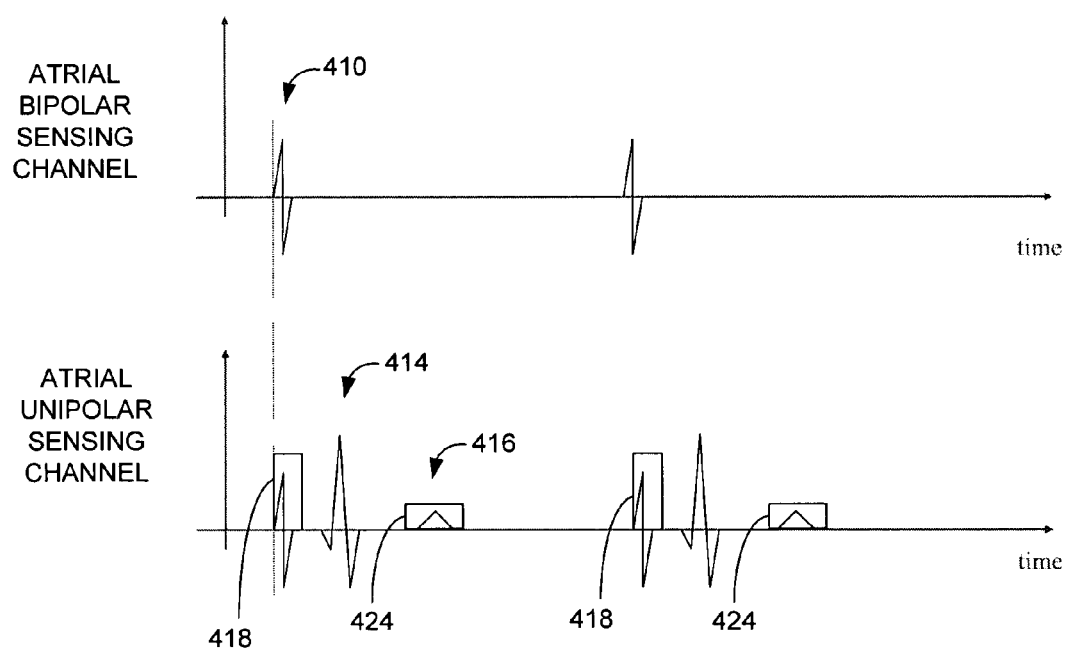
FIG. 9 is a graph illustrating stylized bipolar atrial and unipolar atrial IEGM signals for use with the method of FIG. 7, and particularly illustrating P-wave blanking windows for use in eliminating P-waves from the unipolar channel signals.

Referring now to FIGS. 7–9, the detection of T-waves of step 200 of FIG. 4 will now be described in greater detail. Simultaneously, at steps 400 and 402, atrial near-field signals are received using a bipolar lead mounted within the atria and far-field signals are received via unipolar sensing derived from a lead mounted anywhere in the heart. In one example, the far-field channel is derived via unipolar sensing from a lead mounted in the ventricles (either from a ventricular unipolar lead or from a ventricular bipolar lead used in unipolar configuration). In another example, the far-field channel is derived from an atrial bipolar lead used in unipolar configuration. In other words, in that example, two channels are derived from the single atrial bipolar lead—a near-field channel derived by using the lead in bipolar configuration (i.e. tip to ring sensing) and a far-field channel by using the lead in unipolar configuration (i.e. ring to case sensing.)

In any case, the atrial near-field channel is derived by detecting a voltage difference between a pair of electrodes within the atria; whereas the far-field channel is derived by detecting a voltage difference between an electrode and the device can. The bipolar lead provides a small antenna for detecting electrical signals and is well suited to sensing near-field signals arising within the atria. The large antenna provided via unipolar sensing is well suited for detecting any cardiac electrical cardiac signals, including R-waves and T-waves arising in the ventricles and P-waves arising in atria. This is illustrated within FIG. 8. A graph 408 illustrates surface EKG signals and graph 409 illustrates corresponding atrial bipolar IEGM signals. As can be seen, the bipolar signals contain primarily only P-waves 410. Graph 412 illustrates surface EKG signals and graph 413 illustrates corresponding unipolar channel signals derived from an atrial bipolar lead in a unipolar sensing mode. As can be seen, the unipolar channel signals include R-waves 414 and T-waves 416 as well as P-waves 410. The presence of the P-waves makes it difficult to distinguish between P-waves and R-waves so that the T-waves may be reliably detected.

Figure 10:
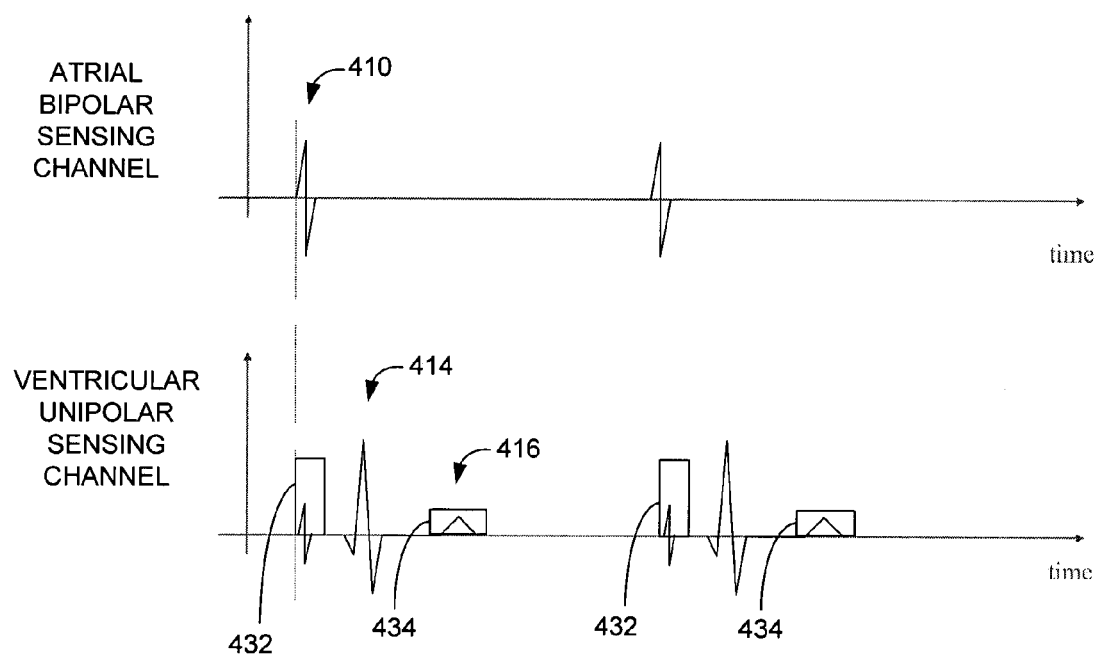
FIG. 10 is a graph illustrating stylized bipolar atrial and unipolar ventricular IEGM signals for use with the method of FIG. 7, and also illustrating P-wave blanking windows for use in eliminating P-waves from unipolar signals.

Returning to FIG. 7, at step 404, the atrial near-field channel signals are examined to detect P-waves therein. The detected P-waves are then used to eliminate or filter P-waves from the far-field unipolar channel signals, at step 406. This is illustrated in FIGS. 9 and 10. FIG. 9 illustrates an atrial bipolar sensing channel along with an atrial unipolar sensing channel derived from the same atrial bipolar lead but operating in a unipolar mode. FIG. 10 illustrates the same atrial bipolar sensing channel along with a ventricular unipolar sensing channel derived from a unipolar lead mounted in the ventricles (or from some other ventricular lead operating in a unipolar mode.) Referring first to FIG. 9, for each P-wave 410 detected within the atrial bipolar signals, an atrial blanking window 418 is applied to the atrial unipolar channel signals. During the blanking window, signals sensed on the atrial unipolar channel are ignored. As a result, only R-waves 414 and T-waves 416 are detected. The R-waves then can be easily distinguished from the T-waves based upon shape and amplitude. Referring next to FIG. 10, for each P-wave 410 detected within the atrial bipolar signals, an atrial blanking window 432 is applied to the ventricular unipolar channel signals so that signals sensed on the ventricular unipolar channel are ignored. As a result, again, only R-waves 414 and T-waves 416 are detected and the R-waves then can be easily distinguished from the T-waves based upon shape and amplitude.

Returning to FIG. 7, the system then detects the peaks of the R-waves and the T-waves within the remaining far-field channel signals, at step 420. For each beat, a T-wave window is calculated, at step 422, based upon either the detected peak of the T-wave or the detected peak of the R-wave. In one example, the device is programmed to specify the T-wave window as commencing 150 milliseconds (ms) prior to the T-wave peak and concluding 150 ms after the T-wave peak. The starting and ending points of the T-wave window are referred to, herein, as $T_{start}$ and $T_{end}$, respectively. Alternatively, the T-wave window is specified as commencing 80 ms after the R-wave peak and terminating 480 ms after the R-wave peak. Preferably, the device is preprogrammed to calculate the T-wave window based on either the T-wave peak or the R-wave peak, but not both. Alternatively, the device may be programmed to utilize the T-wave peak so long as T-waves can be clearly identified and to use the R-wave peak otherwise. Thus, for example, if the amplitudes of the T-waves are relatively low and their peaks cannot be reliably identified, the T-wave window is instead calculated based upon the R-wave peak. Other techniques for specifying the T-wave window may also be employed. For example, the T-wave window may be programmable by the physician via the external programmer. The T-wave window may also be automatically specified based on heart rate or ST interval.

In any case, an exemplary T-wave window 424 applied to the atrial unipolar channel is illustrated within FIG. 9 and an exemplary T-wave window 434 applied to the ventricular unipolar channel is illustrated within FIG. 10. Note that the T-wave windows are not blanking windows during which signals are completely ignored. Rather, the T-wave windows specify periods of time in which the unipolar signals are integrated to determine total T-wave energy and during which time derivatives are calculated to determine T-wave slope. Having determined the T-wave window, processing returns to FIG. 4.

As noted, the improved T-wave detection technique is not limited for use with ischemia detection but may also be used for any other suitable purpose wherein reliable T-wave detection is required, such as in the detection of SVTs and PVCs.

T-Wave Energy and Maximum Slope Calculation

Figure 11:
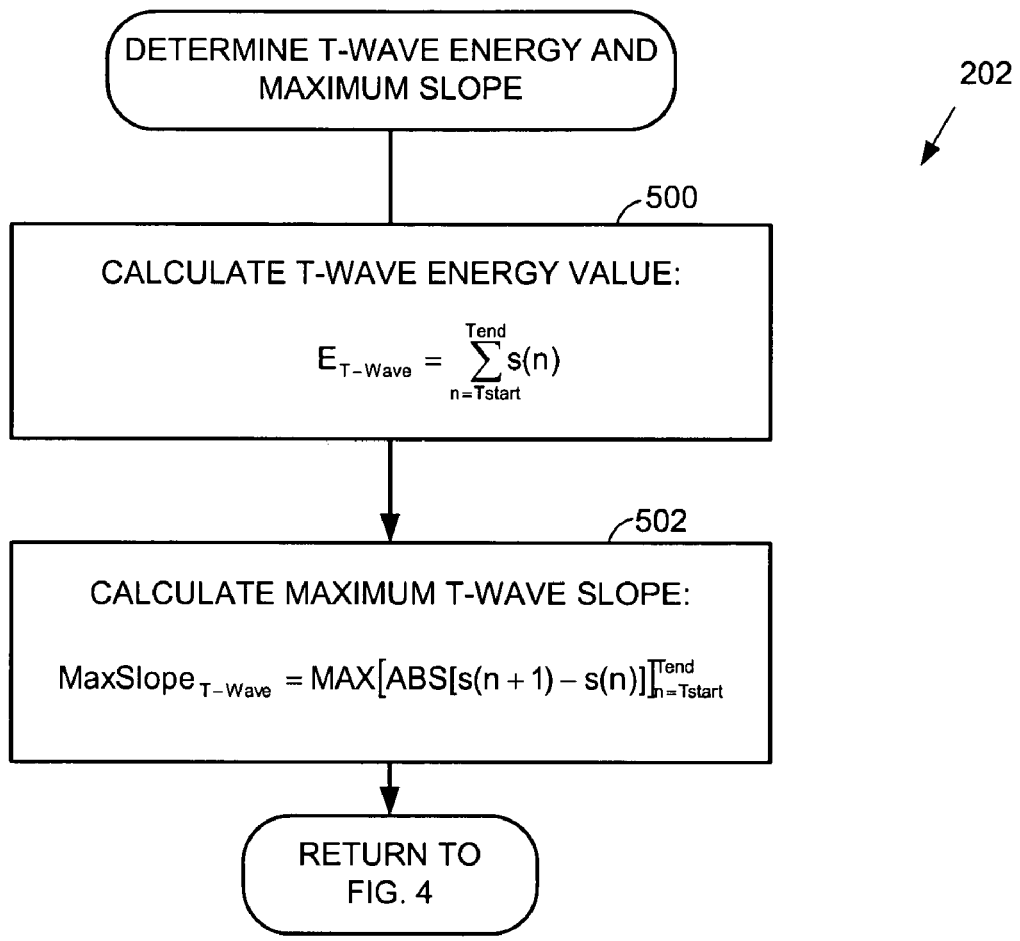
FIG. 11 is a flow chart illustrating an exemplary method for determining T-wave energy and maximum T-wave slope for use with the method of FIG. 4.

Referring now to FIG. 11, the determination of the T-wave energy and maximum slope performed at step 202 of FIG. 4 will now be described in greater detail. At step 500, the total energy of the latest T-wave is calculated based upon the start and stop times of the T-wave window using the following equation:

$$E_{T-Wave} = \sum_{n=Tstart}^{Tend} s(n)$$

wherein s(n) is a digitized version of the cardiac signal and n represents individual samples of a digitized version of an IEGM signal. Only summation is required since the sampling rate is assumed to be fixed. If the sampling rate is not fixed, otherwise conventional signal integration techniques may be used to obtain the T-wave signal energy.

In one example, s(n) is a digitized version of the unipolar ventricular signal filtered using a 0.5 Hz to 40 Hz preamplifier. In other examples, techniques are employed to first emulate a surface EKG based upon IEGM signals, preferably configured to emulate surface leads I, II and V2. The emulated surface EKG is digitized and used as s(n). One technique for emulating a surface EKG using internal electrical signals that allows individual surface EKG lead signals to be individually emulated is described in U.S. patent application Ser. No. 10/334,741 to Kroll et al., entitled "System and Method for Emulating a Surface EKG Using Implantable Cardiac Stimulation Device", filed Dec. 30, 2002, which is assigned to the assignee of the present application and is incorporated by reference herein.

The maximum slope of the T-wave (i.e. max dV/dt) is then calculated, at step 502, using the following equation:

$$MaxSlope_{T-Wave} = MAX[ABS[s(n+1)-n(n)]]_{n=Tstart}^{Tend}$$

i.e. the device calculates the slope at each sample point within the T-wave window by 1) calculating a numerical difference between a pair of adjacent samples at that point; 2) taking absolute values of those differences; and 3) then identifying the maximum of the absolute values. Other techniques may be employed as well. In addition, a maximum positive slope and a maximum negative slope may be separately calculated. In any case, processing again the returns to FIG. 4.

Figure 12:
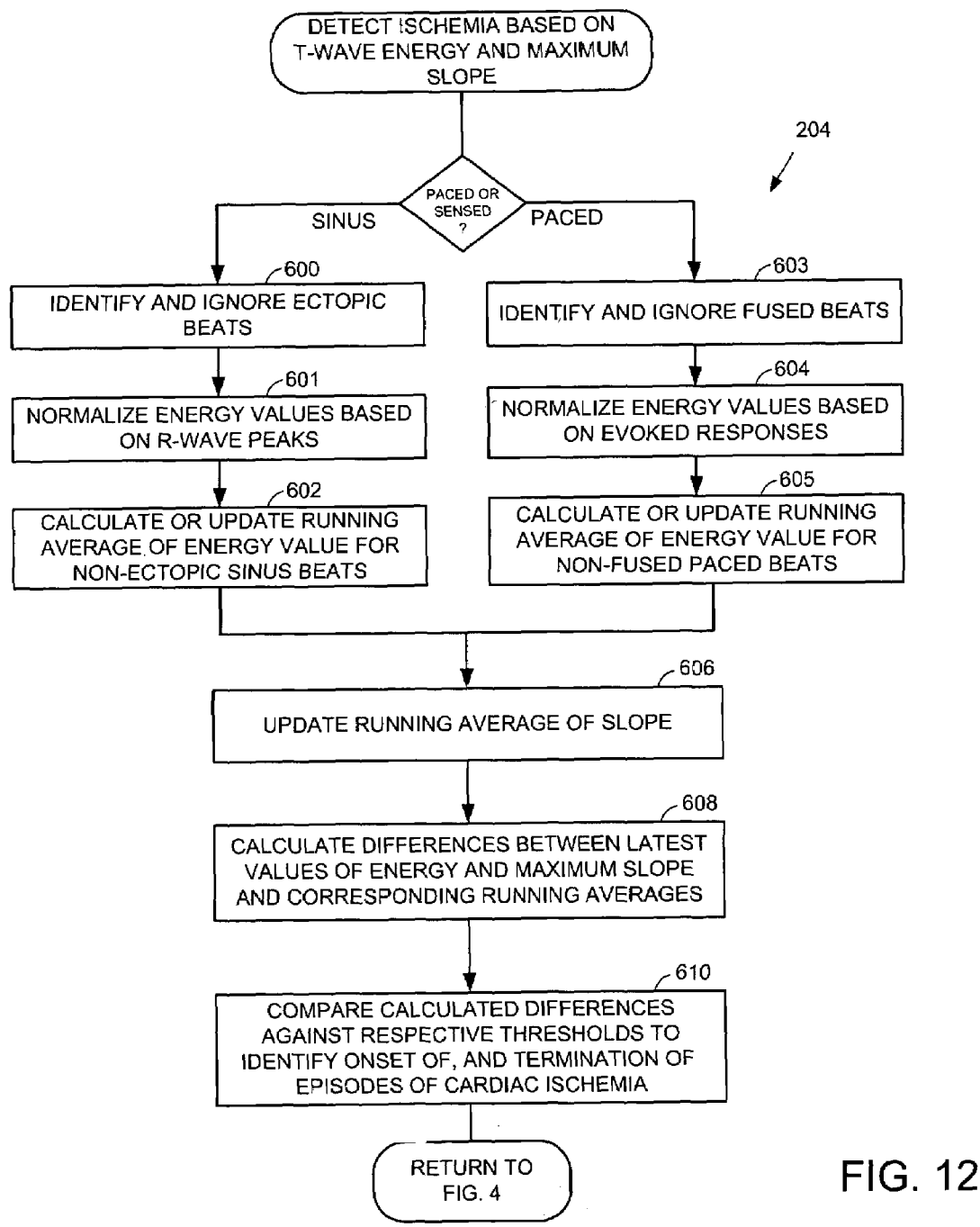
FIG. 12 is a flow chart illustrating an exemplary method for detecting an episode of cardiac ischemia based on whether T-waves are the result of paced beats or sinus beats for use with the method of FIG. 4.

Referring now to FIG. 12, the detection of cardiac ischemia based upon T-wave energy and maximum slope performed at step 204 of FIG. 4 will now be described. As already noted, the detection of ischemia depends, in part, upon whether the latest T-wave is the result of the paced ventricular beat or a sinus ventricular beat. An indication of whether the ventricular beat is paced or not is provided by other components of the microcontroller. If "sinus" then, at step 600, the ischemia detection system first determines whether the T-wave was the result of an ectopic beat and, if so, the T-wave is ignored. To identify ectopic beats, otherwise conventional morphology-based techniques or SVT discrimination techniques can be used. Other suitable techniques can be used as well for detecting ectopic beats such as those described in U.S. Pat. No. 6,081,747 to Levine, et al., which is incorporated by reference herein. Then, at step 601, the detection system normalizes the T-wave energy value (assuming it is not the result of an ectopic beat) based upon the amplitude of the preceding R-wave peak. At step 602, a running average of T-wave energies of all non-ectopic sinus beats is updated ($E_{AverageSinus}$). By normalizing the T-wave energy value, any differences in T-wave energy arising solely from different intrinsic depolarization signal voltages are thereby eliminated.

If "paced", then, at step 603, the detection system first determines whether the T-wave was the result of a fused beat and, if so, the T-wave is ignored. To detect fusion, a paced depolarization integral (PDI) value (or other measure of the evoked response) may be calculated within an evoked response window then compared against acceptable bounds. If the PDI is outside acceptable bounds, then either the paced beat was not captured or fusion occurred. With this technique, a wider than normal evoked response detection window is preferably employed. The size of the window and the acceptable bounds may be determined via routine testing. Other suitable techniques can be used for detecting fusion as well such as those described in U.S. Pat. No. 6,456,881 to Bornzin, et al., which is incorporated by reference herein. Then, at step 604, the detection system then normalizes the T-wave energy value (assuming the T-wave is not ignored) based again on some measure of the evoked response, such as PDI, or on a maximum of the derivative of the evoked response (DMAX). PDI is discussed in U.S. Pat. No. 5,643, 327 to Dawson, et al., which is also incorporated herein by reference. Note that, if the paced beat is not captured, its energy is zero and it is also ignored. At 605, a running average of the normalized T-wave energy for non-fused paced beats is updated ($E_{AveragePaced}$). The corresponding running average is based on some fixed number of previous T-waves, such as the two hundred T-waves. At step 606, a running average of the maximum slope is updated ($E_{AverageMaxSlope}$).

Then, at step 608, differences are calculated between the latest value for the T-wave energy and its corresponding running average and between the latest value of the maximum slope and its corresponding running average. At step 610, the calculated differences are compared against predetermined threshold values ($T_{PacedBeatEnergy}$, $T_{SinusBeatEnergy}$, $T_{MaxSlope}$) to identify the onset of an episode of cardiac ischemia and to subsequently identify the termination of the episode. For example, the following logic may be used to detect the onset of an episode of ischemia:

If "paced" and $E_{T-wave} - E_{AveragePaced} > T_{PacedBeatEnergy}$, or

If "sinus" and $E_{T-wave} - E_{AverageSinus} > T_{SinusBeatEnergy}$, or

If $MaxSlope_{T-wave} - E_{AverageMaxSlope} > T_{MaxSlope}$

Then ischemia is occurring.

The following logic may be used to detect the termination of an episode of ischemia:

If "paced" and $E_{T-wave} - E_{AveragePaced} \leq T_{PacedBeatEnergy}$, or

If "sinus" and $E_{T-wave} - E_{AverageSinus} \leq T_{MaxSlope}$, or

If $MaxSlope_{T-wave} - E_{AverageMaxSlope} \leq T_{MaxSlope}$

Then no ischemia.

Preferably, though, the determination of whether an episode of ischemia has commenced is not based on a single instance of one of the thresholds being exceeded, but is based on some predetermined number of beats for which one or more thresholds is exceeded. A state machine may be employed to implement logic for determining when to enter and when to exit an ischemia alarm state based on some predetermined number of beats for which some combination of thresholds are exceeded. Details of such as state machine may be found in the Wang et al. patent application referenced above. In addition, although described with reference to an example wherein the device examines either T-wave energy or maximum T-wave slope or both, other combinations of features may be exploited. For example, the device may calculate a product of T-wave energy and maximum T-wave slope, which is then compared against suitable thresholds. Alternatively, the average of the slope of the T-wave may instead be exploited. Additionally, or in the alternative, the slope of the ST-segment may be used as a basis for detecting the onset of cardiac ischemia, as it has been found that the slope of the ST-segment is generally elevated during ischemia. Accordingly, either maximum or average slope of the ST-segment (or of a period of time including both the ST-segment and the T-wave) may be examined for the purposes of detecting ischemia.

In general, a wide variety of techniques can be implemented consistent with the principles the invention and no attempt is made herein to describe all possible techniques. Although described primarily with reference to an example wherein the implanted device is a defibrillation/pacer, principles of the invention are applicable to other implantable medical devices as well. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. In an implantable medical device for implant within a patient, a method comprising:
    detecting a plurality of individual T-waves within cardiac signals;
    determining an energy value for each of the plurality of individual T-waves;
    calculating a plurality of slopes for each of the plurality of individual T-waves;
    for each of the plurality of individual T-waves, determining the maximum slope from the plurality of slopes and comparing the maximum slope to a threshold maximum slope and the energy value to a threshold energy value; and
    for each of the plurality of individual T-waves, detecting cardiac ischemia when the energy value and the maximum slope of the T-wave exceeds its respective threshold.

2. The method of claim 1 wherein detecting a plurality of T-waves comprises discarding T-waves associated with one of fusion beats and ectopic beats.

3. The method of claim 1 wherein detecting T-waves comprises:
    sensing bipolar signals using a bipolar lead mounted within the atria and detecting atrial events therein;
    sensing unipolar signals using a unipolar lead mounted within the heart, the unipolar signals having potentially both atrial and ventricular events therein;
    eliminating the atrial events from the unipolar signals to leave substantially only ventricular events therein; and
    examining the ventricular events remaining within the remaining unipolar signals to identify T-waves.

4. The method of claim 1 wherein detecting T-waves comprises:
    identifying peaks of the T-waves; and
    specifying T-wave windows based on the T-wave peaks.

5. The method of claim 4 wherein specifying T-wave windows based on the T-wave peaks comprises:
    identifying a starting point of the T-wave window as commencing 150 milliseconds (ms) prior to a T-wave peak; and
    identifying an ending point of the T-wave window as terminating 150 ms after the T-wave peak.

6. The method of claim 1 wherein detecting T-waves comprises:
    identifying peaks of ventricular depolarization events; and
    specifying T-wave windows based on the depolarization event peaks.

7. The method of claim 6 wherein specifying T-wave windows based on the depolarization event peaks comprises:
    identifying a starting point of the T-wave window as commencing 80 milliseconds (ms) after the depolarization event peak; and
    identifying an ending point of the T-wave window as terminating 480 ms after the depolarization event peak.

8. The method of claim 1 wherein determining energy values associated with the plurality of T-waves comprises calculating:

$$E_{T-Wave} = \sum_{n=Tstart}^{Tend} s(n)$$

wherein s(n) is a digitized version of the cardiac signal, $T_{start}$ and $T_{end}$ are start and end points, respectively, of the T-wave, and n represents individual samples of the digitized version of the cardiac signal.

9. The method of claim 1 further comprising:
detecting a ventricular depolarization event within the cardiac signals that corresponds to the T-wave;
determining whether the T-wave was the result of a paced beat or a sinus beat; and
wherein detecting cardiac ischemia takes into account whether the T-waves are the result of a paced beat or a sinus beat.

10. The method of claim 9 wherein, in response to a sinus beat, detecting cardiac ischemia comprises:
determining a peak amplitude of the depolarization event that corresponds to the T-wave;
normalizing the energy values of the T-waves based on the peak amplitude of the corresponding depolarization event;
determining a running average of normalized energy values of all sinus T-waves;
calculating a difference between a current T-wave energy value and the sinus T-wave running average; and
determining whether the difference exceeds a predetermined sinus beat threshold.

11. The method of claim 10 wherein, in response to a sinus beat, detecting cardiac ischemia comprises:
determining whether the sinus beat is an ectopic beat and, if so, ignoring the T-wave associated with the ectopic beat in the detection of cardiac ischemia.

12. The method of claim 9 wherein, in response to a paced event, detecting cardiac ischemia comprises:
determining a measure of evoked response for the depolarization event that corresponds to the T-wave;
normalizing the energy values of the T-waves based on the evoked response of the corresponding depolarization event;
determining a running average of normalized energy values of paced T-waves;
calculating a difference between a current paced T-wave energy value and the paced T-wave running average; and
determining whether the difference exceeds a predetermined paced beat threshold.

13. The method of claim 12 wherein, in response to a paced event, detecting cardiac ischemia comprises:
determining whether the paced beat is a fused beat and, if so, ignoring the T-wave associated with the fused beat in the detection of cardiac ischemia.

14. The method of claim 1 further comprising:
generating an ischemia warning signal indicative of the onset of ischemia.

15. The method of claim 14 further comprising generating an arrhythmia warning signal indicative of an arrhythmia and having a first stimulation frequency and, wherein the ischemia warning signal is an internal warning signal applied directly to patient tissue and has a stimulation frequency different from the first stimulation frequency.

16. The method of claim 1 wherein products of the energy values and the maximum slopes are used to detect cardiac ischemia.

17. In an implantable medical device for implant within a patient, a system comprising:
means for detecting a plurality of T-waves within cardiac signals;
means for determining energy values associated with the plurality of T-waves;
means for calculating a plurality of slopes for each of the plurality of T-waves and determining a maximum slope for each of the plurality of T-waves from the plurality of slopes associated with the T-wave;
means for comparing the maximum slope of each of the plurality of T-waves to a threshold maximum slope and the energy value of each of the plurality of T-waves to a threshold energy value; and
means for detecting, for each T-wave, cardiac ischemia when the energy value and the maximum slope of the T-wave exceeds its respective threshold.

* * * * *